United States Patent [19]

Wätjen et al.

[11] Patent Number: 4,795,749
[45] Date of Patent: Jan. 3, 1989

[54] IMIDAZOPYRROLOQUINOXALINE COMPOUNDS

[75] Inventors: Frank Wätjen; Mogens Engelstoft, both of Vaerloese, Denmark

[73] Assignee: A/S Ferrosan, Søborg, Denmark

[21] Appl. No.: 108,272

[22] Filed: Oct. 13, 1987

Related U.S. Application Data

[62] Division of Ser. No. 912,776, Sep. 26, 1986.

[30] Foreign Application Priority Data

Oct. 17, 1985 [DK] Denmark .............................. 4768/85

[51] Int. Cl.[4] .................. A61K 31/495; C07D 487/04; C07D 487/14
[52] U.S. Cl. ..................................... 514/250; 544/343
[58] Field of Search ......................... 514/250; 544/343

[56] References Cited

U.S. PATENT DOCUMENTS 4,668,678 5/1987 Brown ................... 544/343

Primary Examiner—Mark L. Berch
Attorney, Agent, or Firm—Gordon W. Hueschen

[57] ABSTRACT

New heterocyclic compounds having the general formula

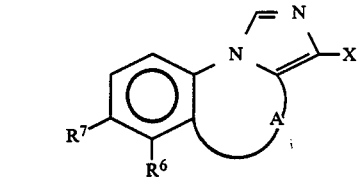

wherein
X is

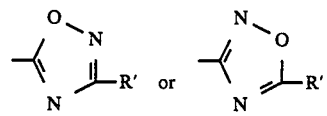

wherein R' is $C_{1-6}$-alkyl, $C_{3-7}$-cycloalkyl, phenyl, thienyl, or $C_{1-3}$-alkoxymethyl,
$R^6$ and $R^7$ independently are hydrogen or halogen, and
—A— is —N(R")—C(O)—, —N(R")—CH$_2$—, or

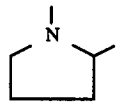

wherein R" is hydrogen, $C_{3-7}$-cycloalkyl, or $C_{1-6}$-alkyl The compounds are useful in psychopharmaceutical preparations as anticonvulsants, anxiolytics, hypnotics, and nootropics.

10 Claims, No Drawings

IMIDAZOPYRROLOQUINOXALINE COMPOUNDS

This is a division of application Ser. No. 912,776, filed Sept. 26, 1986.

The present invention relates to therapeutically active heterocyclic compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732–734) that specific sites in the central nervous systems of vertebrates exhibit a high specific affinity for binding 1,4- and 1,5-benzodiazepines. These sites are called benzodiazepine receptors.

It has now been found that members of a novel group of quinoxaline compounds have strong affinity for the benzodiazepine receptors which make them useful in psychopharmaceutical preparations.

Accordingly, it is an object of the invention to provide such novel quinoxaline compounds.

The quinoxaline compounds of the invention are heterocyclic compounds having the general formula I

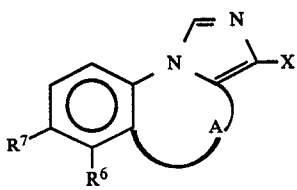

wherein
X is

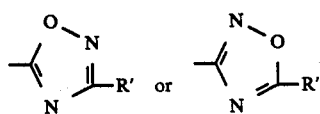

wherein R' is $C_{1-6}$-alkyl, $C_{3-7}$-cycloalkyl, phenyl, thienyl, or $C_{1-3}$-alkoxymethyl, $R^6$ and $R^7$ independently are hydrogen or halogen, and
—A— is —N(R'')—C(O)—, —N(R'')—CH$_2$—, or

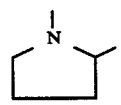

wherein R'' is hydrogen, $C_{3-7}$-cycloalkyl, or $C_{1-6}$-alkyl

The pharmaceutical properties of the compounds of the invention can be illustrated by determining their capability for displacing radioactivity labelled flunitrazepam from benzodiazepine receptors.

The displacement activity of the compounds of the invention may be found by determining the ED$_{50}$ value. The ED$_{50}$ value represents the dose (mg/kg) of a test substance which causes the specific binding of flunitrazepam to benzodiazepine receptors in a living brain to be reduced to 50% of the control value.

Such an in vivo test is carried out as follow:

Principle. Twenty minutes after a dose of $^3$H-flunitrazepam ($^3$H-FNM) (200 μCi/kg, i.v.) the amount of specific $^3$H-FNM binding to brain benzodiazepine receptors has reached its maximum value. This specific binding of $^3$H-FNM can be partly or completely prevented by simultaneous or prior administration of pharmacologically active benzodiazepines and by some benzodiazepine-like agents (Chang and Snyder, Eur.J. Pharmacol. 48, 212–218 (1978)).

Test procedure. Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR, 18–22 gram) are injected with the test substance at 100 mg/kg intraperitoneally. Fifteen minutes after test substance administration the mice are challenged with 4 μCi intravenously of $^3$H-FNM (70–90 Ci/mole) in 200 μl physiological saline. Twenty minutes after $^3$H-FNM administration mice are sacrificed by decapitation, the forebrains rapidly excised (within 30 sec) and homogenized in 12 ml of icecold 25 mM KH$_2$PO$_4$, pH 7.1, using an Ultra-Turrax homogenizer fitted with an N 10 shaft. Two aliquots of 1 ml are immediately filtered through Whatman GF/C glassfiber filters and washed with 2×5 ml of the above mentioned buffer. The amounts of radioactivity on the filters are determined by conventional scintillation counting. One group of untreated mice serves as control. One to three mice are injected with 25 g/kg clonazepam i.p. 30 minutes before $^3$H-FNM to determine the amount of non-specific $^3$H-FNM binding, which should be between 8–15% of total binding. When doses of 100 mg/kg inhibit more than 50% of specific $^3$H-flunitrazepam binding; test substances are administered in doses, which are factors of 3.16 times lower than 100 mg/kg. The ED$_{50}$ for a test substance is defined as that dose which inhibits 50% of specific $^3$H-FNM binding. Specific binding is the amount of binding in controls minus the amount binding in clonazepam-treated mice.

Results. The ED$_{50}$ value is determined from dose response curves. If only one dose of test substance is administered the ED$_{50}$ value is calculated as follows, provided that the inhibition of specific binding is within the range of 25–75%:

$$ED_{50} = \text{(administered dose)} \times \frac{1}{\left(\frac{C_o}{C_x} - 1\right)} \text{ mg/kg}$$

where $C_o$ is specific binding in controls and $C_x$ is specific binding in mice treated with test substance.

Test results obtained by testing a compound of the invention will appear from the following Table I.

TABLE 1

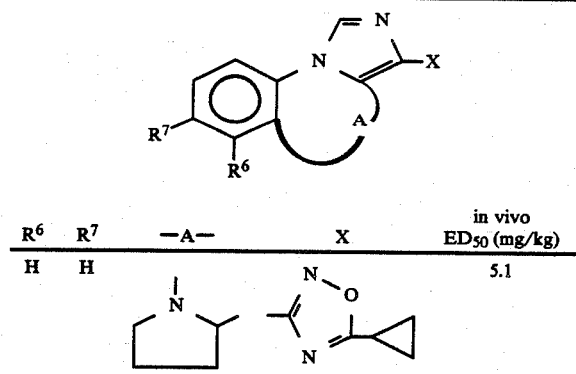

| R⁶ | R⁷ | —A— | X | in vivo ED$_{50}$ (mg/kg) |
|---|---|---|---|---|
| H | H | 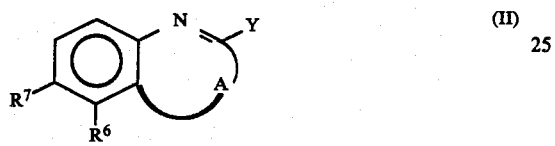 |  | 5.1 |

The invention also relates to a method of preparing the above mentioned compounds. This method comprises:

(a) reacting a compound of formula II

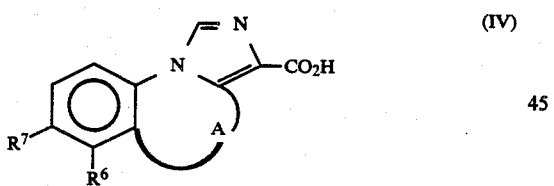

wherein —A—, $R^6$ and $R^7$ have the meanings set forth above and wherein Y is a leaving group, with a compound having the formula III $$CN-CH_2-X \quad \text{(III)}$$

wherein X has the meaning set forth above, to form a compound of the invention, or (b) reacting a reactive derivative of a compound having the general formula IV

wherein —A—, $R^6$ and $R^7$ have the meanings set forth above, with a compound having the general formula V

wherein R' has the meaning set forth above, to form a compound of the general formula I wherein X is

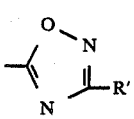

wherein R' has the meaning set forth above, or (c) reacting a compound having the general formula VI

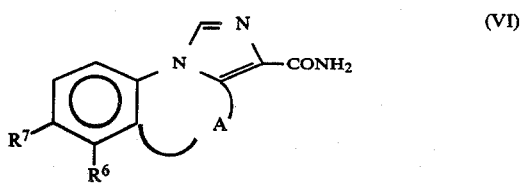

wherein —A—, $R^6$ and $R^7$ have the meanings set forth above, with a compound having the general formula VI $$R'-C(OCH_3)_2N(CH_3)_2 \quad \text{(VII)}$$

wherein R' has the meaning set forth above, to form a compound having the general formula VIII

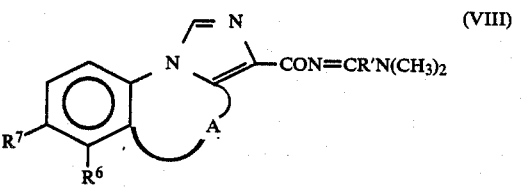

wherein R', —A—, $R^6$ and $R^7$ have the meanings set forth above, and reacting the compound having the formula (VIII) with NH$_2$OH or another aminating agent to form a compound having the generic formula I, wherein X is

wherein R' has the meaning defined above, or (d) reacting a compound having the general formula IX

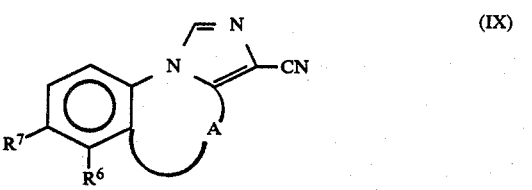

wherein —A—, $R^6$ and $R^7$ have the meanings set forth above, with NH$_2$OH to form a compound having the general formula X

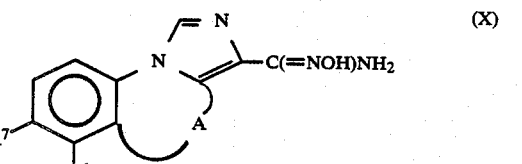

wherein —A— $R^6$ and $R^7$ have the meanings set forth above, and reacting the compound having the formula (X) with R'—COCl, wherein R' has the meaning set forth above, to form a compound of formula I, wherein X is

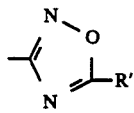

wherein R' has the meaning set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)$_2$ wherein R is lower-alkyl or —OP(O)(NR'R") wherein R' and R" each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available benzene derivatives and by using well known synthetic methods and as described in Synthesis, Vol. 10, pp. 681–682.

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.1–100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the socalled benzodiazepin receptors, which requires such psychopharmaceutical treatment, e.g., especially convulsion and/or nxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1–100 milligrams daily, 1–30 milligrams daily, and especially 1–10 milligrams daily, depending as usual upon the exact mode of administration, form in which administered, the indication toward which the administration is directed, the subject involved and the body weight of the subject involved, and the preference and experience of the physician or veterinarian in charge. Broader ranges for dosages of the compounds according to this invention are 0.1–100 mg/day, preferably 1–30 mg/day, when administered to patients, e.g., humans, as a drug.

The invention will now be described in further detail with reference to the following examples:

EXAMPLE 1

A. 1,2,3,4-tetrahydro-1-methyl-2,3-dioxoquinoxaline

A mixture of 12 g of 98% oxalylchloride in 19.5 ml of triethylamine and 50 ml of toluene was added dropwise to a stirred solution of 8.5 g of o-N-methylamino aniline in 80 ml of toluene. The resulting mixture was heated at reflux for one hour. The precipitate was washed with ether. The residue was stirred with water and filtered to give 1,2,3,4-tetrahydro-1-methyl-2,3-dioxo-quinoxaline.

8-chloro-1,2,3,4-tetrahydro-1-methyl-2,3-dioxoquinoxaline was prepared in exactly the same manner from 3-chloro-o-(N-methylamino) aniline.

1,2,3,4-tetrahydro-1-cyclopropyl-2,3-dioxoquinoxaline was prepared in exactly the same manner from o-N-cyclopropylamino aniline

B. 1,2,3,3a,4,5-hexahydro-4-oxo-pyrrolo(1,2-a)quinoxaline 1.5 ml of o-fluoro-nitrobenzene and 8.2 g of L-proline were stirred at 60° C. for 3 hours in 50 ml DMSO. The mixture was then evaporated in vacuo to give a yellow oil. This oil was dissolved in 250 ml 96% ethanol and was hydrogenated at normal pressure at room temperature using 2 g 5% Pd/C as catalyst. After completion of hydrogen uptake, the mixture was filtered and evaporated in vacuo to give the title compound. M.p. 169°–172° C.

C. Ethyl 4,5-dihydro-5-methyl-4-oxo-imidazo(1,5-a)quinoxaline-3-carboxylate 6.2 ml of diethylchlorophosphate was added to a mixture of 5.3 g of 1,2,3,4-tetrahydro-1-methyl-2,3-dioxo-quinoxaline and of 4.5 g of K-t-butoxide in 50 ml dimethyl formamide (DMF) at room temperature. The resulting mixture was heated until it formed a solution and was then cooled to −30° C. A −30° C. cold mixture of 4.8 g of K-t-butoxide and 4.5 ml of ethyl isocyanoacetate in 20 ml of dry DMF was added to this solution. The resulting mixture was stirred for one hour at room temperature. Then 100 ml of water was added and the mixture was filtered. The resulting residue was crystallized leaving 2.5 g of the title compound. M.p. 218.5°–219.8° C.

Ethyl 10,11,12,12a-tetrahydro-imidazo(1,5-a)pyrrolo(2,1-c)quinoxaline-1-carboxylate, M.p. 163.6°–164.4° C., was prepared in exactly the same manner from 1,2,3,-a,4,5-hexahydro-4-oxo-pyrrolo(1,2-c)quinoxaline.

Ethyl 6-chloro-4,5-dihydro-5-methyl-4-oxoimidazo(1,5-a)quinoxaline-3-carboxylate, M.p. 179° C., was prepared in exactly the same manner from 8-chloro-1,2,3,4tetrahydro-1-methyl-2,3-dioxoquinoxaline.

D. Methoxyacetamide oxime 2.3 g of sodium in 33 ml of dry methanol was mixed with 6.55 g of hydroxylamine hydrochloride in 66 ml of dry methanol. The mixture was filtered and 7.8 g of methoxyacetonitrile was added dropwise to the filtrate. The mixture was left for 48 hours at room temperature. The mixture was then cooled to 4° C. Filtration and evaporation of the filtrate give 8.7 g of the title compound.

The following compounds were synthesized from the appropriate nitriles in an analogous manner:
Propionamide oxime
Cyclopropyl carboxamide oxime
2-thienyl carboxamide ixime
benzamide oxime
acetamideoxime

E. 3-(3-cyclopropyl-1,2,4-oxadiazol-5-yl)-4,5-dihydro-5-methyl-4-oxo-imidazo(1,5-a)quinoxaline 50 mg of sodium was dissolved in 25 ml of dry ethanol containing 3 g of molecular sieves (4 Å) and 0.5 g of cyclopropylcarboxamide oxime was added to this mixture and thereupon 0.6 g of ethyl 4,5-dihydro-5-methyl-4-oxo-imidazo(1,5-a)quinoxaline-3-carboxylate. The resulting mixture was refluxed for 2 hours, whereafter the molecular sieves were filtered off. The title compound was isolated after evaporation of the solvent in vacuo, followed by addition of icewater and filtration. yield 0.4 g of title compound. M.p. 224.7°–225.6° C.

In the same manner the following compounds were synthesized:
3-(3-methoxymethyl-1,2,4-oxadiazol-5-yl)-4,5-dihydro-5-methyl-4-oxo-imidazo(1,5-a)quinoxaline, M.p. 184°–190° C. by reaction between ethyl 4,5-dihydro-5-methyl-4-oxo-imidazo(1,5-a)quinoxaline-3-carboxylate and methoxyacetamide oxime.
3-(3-cyclopropyl-1,2,4-oxadiazol-5-yl)-4,5-dihydro-5-methyl-6-chloro-4-oxo-imidazo(1,5-a)quinoxaline, M.p. 216.5°–218.4° C. by reaction between ethyl 6-chloro-4,5-dihydro-5-methyl-4-oxo-imidazo(1,5-a)quinoxaline-3-carboxylate and cyclopropyl carboxamide oxime.
1-(3-ethyl-1,2,4-oxadiazol-5-yl)-10,11,12,12a-tetrahydroimidazo(1,5-a)pyrrolo(2,1-c)quinoxaline, M.p. 123°–124.9° C., by reaction between ethyl 10,11,12,12a-tetrahydro-imidazo(1,5-a)pyrrolo(2,1-c)quinoxaline and propionamide oxime.
1-(3-cyclopropyl-1,2,4-oxadiazol-5-yl)-10,11,12,12a-tetrahydro-imidazo(1,5-a)pyrrolo(2,1-c)quinoxaline, M.p. 142.5° C. by reaction between ethyl 10,11,12,12a-tetrahydro-imidazo(1,5-a)pyrrolo(2,1-c)quinoxaline and cyclopropyl carboxamide oxime.
1-(3-phenyl-1,2,4-oxadiazol-5-yl)-10,11,12,12a-tetrahydroimidazo(1,5-a)pyrrolo(2,1-c)quinoxaline, M.p. 195°–200° C., by reaction between ethyl 10,11,12,12a-tetrahydro-imidazo(1,5-a)pyrrolo(2,1-c)quinoxaline and benzamide oxime.
1-(3-(2-thienyl)-1,2,4-oxadiazol-5-yl)-10,11,12,12a-tetrahydro-imidazo(1,5-a)pyrrolo(2,1-c)quinoxaline, M.p. 175.2°–176.6° C., by reaction between ethyl 10,11,12,12a-tetrahydroimidazo(1,5-a)pyrrolo(2,1-c)quinoxaline and 2-thienyl carboxamide oxime.

EXAMPLE 2

A. 3-cyclopropyl-5-isocyanomethyl-1,2,4-oxadiazole a. 3-cyclopropyl-5-formylaminomethyl-1,2,4-oxadiazole.

A solution of ethyl formylaminomethyl-carboxylate (150 mmol) and cyclopropyl carboxamide oxime (100 mmol) in 100% EtOH (100 ml) was charged with Na (200 mg) and crushed molecular sieve (4 Å) (10 g). The mixture thus obtained was stirred and heated to reflux for 16 hours. The mixture was cooled to room temperature, filtered through filter aid and the filtrate was evaporated in vacuo. The oily residue was partitioned into a CHCl$_3$ phase which was dried with Na$_2$SO$_4$ and evaporated to give the title compound as an oil.

b. 3-cyclopropyl-5-isocyanomethyl-1,2,4-oxadiazole.

A stirred solution of 3-cyclopropyl-5-formylaminomethyl-1,2,4-oxadiazole (60 mmol) and triethylamine (176 mmol) in CH$_2$Cl$_2$ (100 ml) was charged dropwise with POCl$_3$ (60 mmol) at 0° C. The mixture was then left for 30 minutes with stirring at 0° C., whereafter a solution of Na$_2$CO$_3$ (60 mmol) in H$_2$O (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 cm$^{-1}$.

3-ethyl-5-isocyanomethyl-1,2,4-oxadiazole was prepared from 3-ethyl-5-formylaminomethyl-1,2,4-oxadiazole in a similar manner. IR: cm$^{-1}$: 2170.

B. 5-cyclopropyl-3-isocyanomethyl-1,2,4-oxadiazole a. Formylaminomethyl-carboxamide oxime.

0.55 mmol of freshly liberated hydroxylamine dissolved in 370 ml methanol was added to 53.6 g (0.638 mmol) N-formylamino-acetonitrile. An ice bath was used to keep the temperature below 20° C. during addition. The solution was allowed to stand at room temperature overnight, whereafter it was evaporated to give the title compound as pale crystals. Decomp. 104°–110° C.

b. 3-formylaminomethyl-5-cyclopropyl-1,2,4-oxadiazole

A mixture of 35 ml ethyl cyclopropylcarboxylate, 20 g formylamino-methylcarboxamide oxime, 1 g sodium and 30 g of crushed molecular sieve (4 Å) was refluxed in 300 ml abs. EtOH for 8 hours whereafter a further 1 g sodium was added.

The reaction mixture was filtered and the filtrate was evaporated. The dark oily residue was suspended in 300 ml CHCl$_3$, filtered and the filtrate was evaporated to give the title compound as an oil. H-NMR (60 MHz, CDCL$_3$) (ppm): 1.2 (4H, m), 2.8 (1H, m), 4.5 (2H, d, J=6 Hz), 7.8 (1H, broad-NH), 8.2 (1H, s).

The following compounds were synthesized from the appropriate ethyl esters in a similar manner:

3-Formylaminomethyl-5-ethyl-1,2,4-oxadiazole. H-NMR(60 MHz, CDCl$_3$) (ppm) 1.4 (3H, t, J=8 Hz), 2.9 (2H, q, J=8 Hz) 4.55 (2H, s), 7.8 (1H, broad-NH), 8.25 (1H, s).

3-Formylaminomethyl-5-methyl-1,2,4-oxadiazole. H-NMR (60 MHz, CDCl$_3$) (ppm); 2.6 (3H, s), 4.6 (2H, d, J=3 Hz), 7.4 (1H, broad-NH), 8.25 (1H, s).

3-Formylaminomethyl-5-methoxymethyl-1,2,4-oxadiazole H-NMR (60 MHz, CDCl) (ppm): 3.5 (3H, s), 4.7 (4H, s+d, J=6 Hz), 7.8 (1H, broad-NH), 8.25 (H, s).

c. 5-Cyclopropyl-3-isocyanomethyl-1,2,4-oxadiazole

A stirred solution of 5-cyclopropyl-3-formylaminomethyl-1,2,4-oxadiazole (60 mmol) and triethylamine (176 mmol) in CH$_2$Cl$_2$ (100 ml) was charged dropwise with POCl$_3$ (60 mmol) at 0° C. The mixture was then left for 30 minutes with stirring at 0° C., whereafter a solution of 60 mmol) in H$_2$O (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 cm$^{-1}$.

5-Ethyl-3-isocyanomethyl-1,2,4-oxadiazole, 5-methyl-3-isocyanomethyl-1,2,4-oxadiazole, and 5-methoxymethyl-3-isocyanomethyl-1,2,4-oxadiazole were prepared in a similar manner. All compounds were oils and were characterized by their IR stretching band at 2160 cm$^{-1}$.

C. 1,2,3,4-tetrahydro-1-methyl-3-oxo-quinoxaline 5.2 g of o-fluoro-nitrobenzene, 3.2 g of sarcosine and 5.2 ml triethylamine was stirred in 25 ml DMSO at 70° C. for 4 days. The mixture was then evaporated in vacuo and the residue was partitioned between water and methylene chloride. The organic phase was evaporated in vacuo. The residue was dissolved in 100 ml 96% ethanol and was hydrogenated at normal pressure using 0.5 g Pd/C. After completion of hydrogen uptake, the mixture was filtered and evaporated in vacuo. The residue was washed with water with disodium carbonate, ether and water. yield of title compound: 1.3 g M.p. 132° C.

D. 3-(5-cyclopropyl-1,2,4-oxadiazol-3-yl)-4,5-dihydro-4-oxo-5-methyl-imidazo(1,5-a)quinoxaline.

1.7 ml of diethylchlorophosphate was added to a mixture of 1.8 g of 1,2,3,4-tetrahydro-1-methyl-2,3-dioxo-quinoxaline and of 12 mmol sodium hydride in 15 ml dry dimethyl formamide (DMF) at room temperature. The resulting mixture was heated until a clear solution had formed. The solution was then cooled to −30° C. A −30° C. cold mixture of 1.35 g of K-t-butoxide and 1.8 g of 3-isocyanomethyl-5-cyclopropyl-1,2,4-oxadiazole in 10 ml DMF was added to this solution at −10° to −20° C. The resulting mixture was left overnight at 4 degrees C. Three (3) ml of glacial acetic acid was added and the mixture was poured into water and was then filtered. The product was washed with ethyl acetate giving 150 mg of the title compound. M.p. 284.2°–288.2° C.

The following compounds were prepared in exactly the same manner:

1-(5-cyclopropyl-1,2,4-oxadiazol-3-yl)-10,11,12,12a-tetrahydro-imidazo(1,5-a)pyrrolo(2,1-c)quinoxaline, M.p. of the hydrochloride 190°–200° C., by reaction between 1,2,3,3a,4,5-hexahydro-4-oxo-pyrrolo(1,2-a)quinoxaline and 5-cyclopropyl-3-isocyanomethyl-1,2,4-oxadiazole.

1-(5-methyl-1,2,4-oxadiazol-3-yl)-10,11,12,12a-tetrahydroimidazo(1,5-a)pyrrolo(2,1-c)quinoxaline, M.p. 146.4°–148.5° C., by reaction between 1,2,3,3a,4,5-hexahydro-4-oxo-pyrrolo(1,2-a)quinoxaline and 5-methyl-3-isocyanomethyl-1,2,4-oxadiazole.

3-(5-cyclopropyl-1,2,4-oxadiazol-3-yl)-4,5-dihydro-5-methylimidazo(1,5-a)quinoxaline, M.p. of hydrochloride 275°–280° C., by reaction between 1,2,3,4-tetrahydro-1-methyl-3-oxo-quinoxaline and 5-cyclopropyl-3-isocyanomethyl-1,2,4-oxadiazole.

3-(5-cyclopropyl-1,2,4-oxadiazol-3-yl)-4,5-dihydro-5-cyclopropyl imidazo(1,5-a)quinoxaline, M.p. of hydrochloride 290°–300° C., by reaction between 1,2,3,4-tetrahydro-1-cyclopropyl-3-oxo-quinoxaline and 5-cyclopropyl-3-isocyanomethyl-1,2,4-oxadiazole.

In conclusion from the foregoing, it is apparent that the present invention provides novel neurologically-effective benzodiazepine receptor binding compounds and salts thereof, having advantageous and unpredictable properties, as well as novel pharmaceutical compositions thereof and a method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. Heterocyclic quinoxaline compounds having formula I

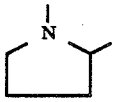

wherein
X is

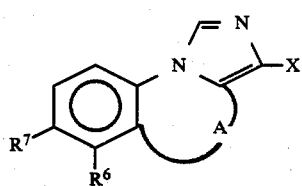

wherein R' is $C_{1-6}$-alkyl, $C_{3-7}$-cycloalkyl, phenyl, thienyl, or $C_{1-3}$-alkoxymethyl,
$R^6$ and $R^7$ independently are hydrogen or halogen, and
—A— is

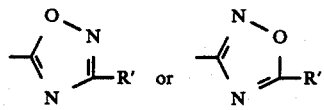

2. A compound of claim 1 which is 1-(5-methyl-1,2,4-oxadiazol-3-yl)-10,11,12,12a-tetrahydro-imidazo(1,5pyrrolo(2,1-c)quinoxaline.

3. A pharmaceutical composition suitable for use in the treatment of a central nervous system ailment selected from convulsion and anxiety comprising an amount of a compound of a compound of claim 1 which is effective for the alleviation of such disorder together with a pharmaceutically-acceptable carrier or diluent.

4. A pharmaceutical composition according to claim 3 in the form of an oral dosage unit containing 1–100 mg of the active compound.

5. A method of treating a central nervous system ailment in a subject in need of such treatment comprising the step of administering to said subject an amount af a compound of claim 1 which is effective for the alleviation of such ailment selected from convulsion and anxiety.

6. A method of treating a central nervous system ailment selected from convulsion and anxiety in a subject in need of such treatment comprising the step of administering to said subject an amount of a compound of claim 1 which is effective for the alleviation of such ailment in the form af a pharmaceutical composition thereof, in which it is present together with a pharmaceutically-acceptable carrier or diluent.

7. A compound of claim 1 which is 1-(3-(2-thienyl)-1,2,4-oxadiazol-5-yl)-10,11,12,12a-tetrahydro-imidazo(1,5-a) pyrrolo(2,1-c)quinoxaline.

8. A compound of claim 1 which is 1-(5-cyclopropyl-1,2,4-oxadiazol-3-yl)-10,11,12,12a-tetrahydro-imidazo(1,5-a)pyrrolo(2,1-c)quinoxaline.

9. A compound of claim 1 which is 1-(3-cyclopropyl-1,2,4-oxadiazol-5-yl)-10,11,12,12a-tetrahydro-imidazo(1,5-a) pyrrolo(2,1-c)quinoxaline.

10. A compound of claim 1 which is 1-(3-phenyl-1,2,4-oxadiazol-5-yl)-10,11,12,12a-tetrahydro-imidazo(1,5-a) pyrrolo(2,1-c) quinozaline.

* * * * *

UNITED STATES PATENT AND TRADEMARK OFFICE
CERTIFICATE OF CORRECTION

PATENT NO. : 4,795,749
DATED : January 3, 1989
INVENTOR(S) : Frank Wätjen and Mogens Engelstoft It is certified that error appears in the above-identified patent and that said Letters Patent is hereby corrected as shown below:

Title Page, [62] Related U.S. Application Data; after "Sep. 26, 1986" insert -- , now U.S. Patent No. 4,774,245, issued Sep. 27, 1988 --
Title Page, [56] References Cited, U.S. PATENT DOCUMENTS; "Brown" should read -- Brown et al. --
Col. 1, line 6; after "1986" insert -- , now U.S. Patent No. 4,774,245, issued Sept. 27, 1988 --
Col. 2, line 1; "follow:" should read -- follows: --
Col. 2, line 6; "maximum" should read -- maximal --
Col. 4, line 66; "-A- $R^6$" should read -- -A-, $R^6$ --
Col. 5, line 59; "to hundred" should read -- to one hundred --
Col. 6, line 53; "socalled" should read -- so-called --
Col. 6, line 55; "nxiety" should read -- anxiety --
Col. 7, line 64; "1,2,3,-a,4,5-" should read -- 1,2,3,3a,4,5- --
Col. 8, line 1; "-1,2,3,4tetrahydro-" should read -- -1,2,3,4-tetrahydro- --
Col. 8, line 34; "yield" should read -- Yield --
Col. 8, line 67; "-tetrahydroimidazo" should read -- -tetrahydro-imidazo --
Col. 9, line 61; "(ppm) 1.4" should read -- (ppm): 1.4 --
Col. 10, line 9; "of 60" should read -- of $Na_2CO_3$ (60 --
Col. 10, line 35; "yield" should read -- Yield --
Col. 10, line 65; "droimidazo" should read -- dro-imidazo --
Col. 12, approx. line 11; The end of Claim 1 should have a period -- . -- inserted after the formula.
Col. 12, line 15; "5pyrrolo" should read -- 5-a) pyrrolo --

UNITED STATES PATENT AND TRADEMARK OFFICE
CERTIFICATE OF CORRECTION

PATENT NO. : 4,795,749

DATED : January 3, 1989

INVENTOR(S) : Frank Wätjen and Mogens Engelstoft

It is certified that error appears in the above-identified patent and that said Letters Patent is hereby corrected as shown below:

```
Col. 12, line 28; "af" should read -- of --
Col. 12, line 36; "af" should read -- of --
Col. 12, line 50; "quinozaline." should read -- quinoxaline. --
```

Signed and Sealed this

Fifteenth Day of August, 1989

Attest:

DONALD J. QUIGG

Attesting Officer

Commissioner of Patents and Trademarks